United States Patent
Bezalel et al.

(10) Patent No.: US 11,571,568 B2
(45) Date of Patent: Feb. 7, 2023

(54) DERMATOLOGICAL ELECTROPORATION DEVICES AND METHODS

(71) Applicant: Mayo Foundation for Medical Education and Research, Rochester, MN (US)

(72) Inventors: Spencer A. Bezalel, Rochester, MN (US); Clark C. Otley, Rochester, MN (US); Samuel J. Asirvatham, Rochester, MN (US); Christian Lee Baum, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 136 days.

(21) Appl. No.: 17/058,419

(22) PCT Filed: Jun. 10, 2019

(86) PCT No.: PCT/US2019/036311
§ 371 (c)(1),
(2) Date: Nov. 24, 2020

(87) PCT Pub. No.: WO2019/237107
PCT Pub. Date: Dec. 12, 2019

(65) Prior Publication Data
US 2021/0187287 A1 Jun. 24, 2021

Related U.S. Application Data

(60) Provisional application No. 62/682,522, filed on Jun. 8, 2018.

(51) Int. Cl.
*A61N 1/32* (2006.01)
*A61N 1/20* (2006.01)

(52) U.S. Cl.
CPC ............... *A61N 1/328* (2013.01); *A61N 1/20* (2013.01); *A61N 1/327* (2013.01)

(58) Field of Classification Search
CPC .......... A61N 1/328; A61N 1/20; A61N 1/327; A61N 1/0502; A61M 35/00
See application file for complete search history.

(56) References Cited

U.S. PATENT DOCUMENTS 7,979,117 B2   7/2011   Mavor et al.
8,588,884 B2   11/2013  Hegde et al.
(Continued)

FOREIGN PATENT DOCUMENTS

EP   1059960   12/2004

OTHER PUBLICATIONS

Bikle et al., "Calcium regulation of keratinocyte differentiation," Exp. Rev. Endocrinol. Metabolism, Jul. 2012, 7(4):461-472.
(Continued)

*Primary Examiner* — Mark W. Bockelman
(74) *Attorney, Agent, or Firm* — Fish & Richardson P.C.

(57) ABSTRACT

Devices and methods can be used to treat dermatologic disorders, hyperhidrosis, and wrinkles using DC electroporation. In some cases, such electroporation is essentially non-thermal modulation that can be used to ablate keratinocyte neoplasms, such as seborrheic keratosis, and other non-keratinocyte derived neoplasms of the skin and adnexal structures and related structures in other anatomic sites. In some implementations, the devices and methods described herein can be used for therapy delivery for the treatment of early or pre-malignant skin cancers. In some implementations, the devices and methods described herein can be used for treatment of hyperhidrosis and cosmetic issues.

12 Claims, 1 Drawing Sheet

(56) References Cited

U.S. PATENT DOCUMENTS

| 9,186,490 B2 | 11/2015 | Chang et al. |
| 2010/0210994 A1 | 8/2010 | Zarif |
| 2011/0009807 A1 | 1/2011 | Kjeken et al. |
| 2013/0150935 A1 | 6/2013 | Weissberg et al. |
| 2014/0378887 A1 | 12/2014 | Chang et al. |
| 2015/0133906 A1 | 5/2015 | Horton et al. |
| 2018/0071014 A1 | 3/2018 | Neal et al. |

OTHER PUBLICATIONS

Frandsen et al., "Normal and Malignant Cells Exhibit Differential Responses to Calcium Electroporation," Cancer Research, Jul. 31, 2017, 77(16):4389-4401.
Goldberg et al., "Skin Rejuvenation with Non-Invasive Pulsed Electric Fields," Sci. Reports, May 12, 2015, 5:10187, 18 pages.
Kaufman et al., "A Dose-Response Study of a Novel Non-Thermal Method of Selectively Modifying Cellular Structures in Skin with Low Energy Nanosecond Electrical Stimulation," Presented at Proceedings of the American Society for Laser Medicine and Surgery Annual Meeting, Dallas, TX, USA, Apr. 11-15, 2018, 5 pages.
PCT International Preliminary Report on Patentability in International Appln. No. PCT/US2019/036311, dated Dec. 8, 2020, 6 pages.
PCT International Search Report and Written Opinion in International Appln. No. PCT/US2019/036311, dated Aug. 22, 2019, 8 pages.
Rohrer et al.. "First Clinical Use of Non-Thermal Nano-Pulse Stimulation to Eliminate Seborrheic Keratosis Lesions," Presented at Proceedings of the American Society for Laser Medicine and Surgery Annual Meeting, Dallas, TX, USA, Apr. 11-15, 2018, 4 pages.

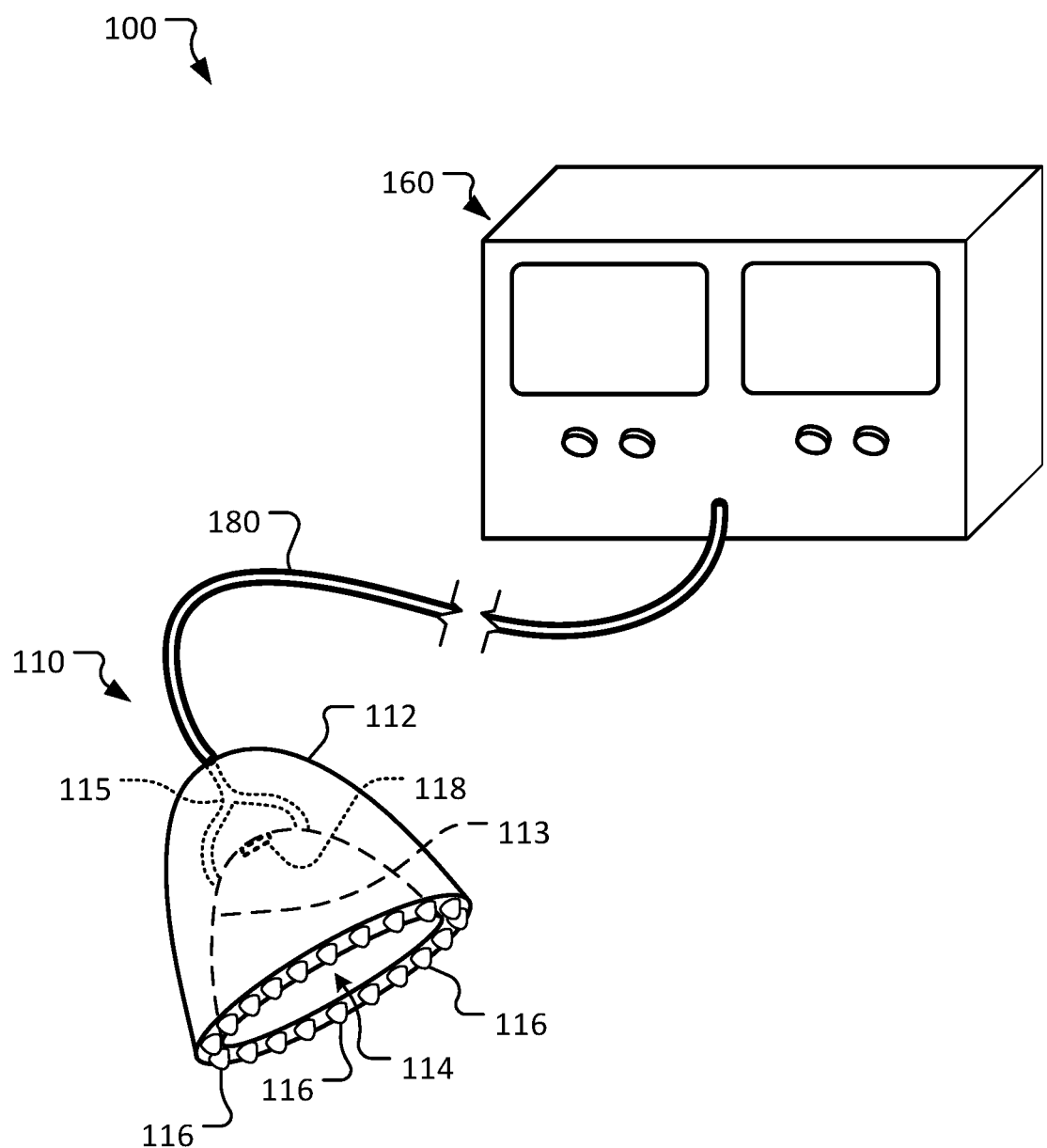

DERMATOLOGICAL ELECTROPORATION DEVICES AND METHODS

CROSS-REFERENCE TO RELATED APPLICATIONS

This application is a National Stage application under 35 U.S.C. § 371 of International Application No. PCT/US2019/036311, having an International Filing Date of Jun. 10, 2019, which claims priority to U.S. Application Ser. No. 62/682,522, filed on Jun. 8, 2018. The disclosure of the prior application is considered part of the disclosure of this application, and is incorporated in its entirety into this application.

BACKGROUND

1. Technical Field

This document relates to devices and methods for treating skin disorders and other conditions such as hyperhidrosis, and cosmetic issues such as skin wrinkles. For example, this document relates to devices and methods for treating dermatologic disorders, hyperhidrosis, and wrinkles using non-thermal irreversible or reversible electroporation.

2. Background Information

Seborrheic keratosis are ubiquitous in humans with 80-100% of people over the age of 50 years old developing one. Many people have numerous seborrheic keratosis, with some people even having hundreds. They are a benign skin tumor that many people seek treatment for due to their cosmetically displeasing appearance or irritation caused by trauma. Current treatments include shave removal, excision, cryotherapy, curettage, electrodessication, and other destructive methods.

Each year there are increasing numbers of new cases of skin cancer than the combined incidence of cancers of the breast, prostate, lung, and colon. The annual cost of treating skin cancers in the U.S. is estimated at $8.1 billion; about $4.8 billion for non-melanoma skin cancers and $3.3 billion for melanoma.

Skin cancer develops from uncontrolled growth of abnormal skin cells. It can occur when skin cell DNA is damaged and/or remains unrepaired (most often caused by ultraviolet radiation from sunrays or tanning beds). This can trigger mutations, or genetic defects in the DNA, that lead the skin cells to multiply rapidly and form malignant tumors. Skin cancers found and removed early can be curable. The types of skin cancers and pre-cancers include actinic keratosis, basal cell carcinoma, melanoma, Merkel cell carcinoma, squamous cell carcinoma and other benign and malignant tumors of adnexal origin.

SUMMARY

This document describes devices and methods for treating skin disorders and other conditions such as hyperhidrosis, and cosmetic issues such as skin wrinkles. For example, this document describes devices and methods for treating dermatologic disorders, hyperhidrosis, and wrinkles using non-thermal irreversible or reversible electroporation. Such irreversible electroporation can be used to ablate keratinocyte neoplasms, such as seborrheic keratosis, nevomelanocytic tumors, and other non-keratinocyte derived neoplasms of the skin and adnexal structures and related structures in other anatomic sites. In some implementations, the devices and methods described herein can be used for early detection of skin cancers. In some implementations, the devices and methods described herein can be used for therapy delivery for the treatment of early or pre-malignant skin cancers. In some implementations, the devices and methods described herein can be used for treatment of hyperhidrosis.

Electroporation is a technology that applies pulsed electrical fields to a target tissue resulting in the formation of pores in the cellular membrane. Reversible electroporation occurs when the electrical field applied results in transient pore formation in the cellular membrane that the cell can later repair. Reversible electroporation does not result in cell death, but is typically utilized to deliver drugs or vaccination to target cells. Irreversible electroporation occurs when the magnitude of the electrical field applied causes the formation of permanent pores in the cell membrane resulting in death of the cell.

In one aspect, this disclosure is directed to a skin treatment system that includes an electroporation applicator and a controller. The electroporation applicator can include a suction head with a concave surface defining an internal space, and a plurality of protrusions disposed around an external periphery of the internal space. Each protrusion can include a respective electrode mounted thereto. The controller can be in communication with the electroporation applicator via one or more cables. The controller can be configured to concurrently: (i) provide direct current electroporation energy to the electrodes mounted on the protrusions and (ii) draw a vacuum in the internal space of the suction head.

Such a skin treatment system may optionally include one or more of the following features. The system may also include one or more additional electrodes on the concave surface. The system may also include a temperature sensor coupled to the electroporation applicator that is configured for measuring a temperature of skin to which the suction head is abutting. The system may also include a humidity sensor coupled to the electroporation applicator. In some embodiments, the plurality of protrusions are height adjustable. The size of the internal space may be adjustable. The system may also include a divider within the internal space that is configured to split the internal space into two or more portions.

In another aspect, this disclosure is directed to a method for treating a patient. The method includes positioning a skin treatment system in contact with skin of the patient. The skin treatment system includes: (1) an electroporation applicator comprising a suction head with a concave surface defining an internal space and a plurality of protrusions disposed around an external periphery of the internal space, each protrusion including a respective electrode mounted thereto; and (2) a controller in communication with the electroporation applicator via one or more cables, the controller configured to concurrently: (i) provide direct current electroporation energy to the electrodes mounted on the protrusions and (ii) draw a vacuum in the internal space of the suction head. The method also includes drawing vacuum in the internal space of the suction head such that skin of the patient is sucked into the internal space; and while drawing the vacuum, delivering DC electroporation energy to the skin of the patient from the electrodes on the plurality of protrusions.

Such a method for treating a patient may optionally include one or more of the following features. The method may also include, contemporaneously with drawing the vacuum and delivering the DC electroporation energy, measuring, by the controller, inter-electrode impedance. The method may also include modulating, by the controller and in response to the measured inter-electrode impedance, the delivery of the DC electroporation energy. The method may also include, contemporaneously with drawing the vacuum and delivering the DC electroporation energy, measuring, by the controller, temperature of the skin of the patient. The method may also include modulating, by the controller and in response to the measured temperature of the skin of the patient, the delivery of the DC electroporation energy.

Particular embodiments of the subject matter described in this document can be implemented to realize one or more of the following advantages. In some implementations, the devices and methods described herein can be utilized by a user at an in-home setting. Accordingly, the frequency of use and regularity of use can be enhanced in comparison to purely clinical or in the clinic treatments. Such increased regularity of use can be advantageously effective for increasing compliance, as well as enhancing chronic therapy delivery. Users can advantageously treat lesions in a short amount of time, or a longer amount of time depending on the clinical situation. The systems and methods described herein can deliver painless therapy, scar-less therapy, and low cost therapy. In addition, in some implementations, the devices and methods described herein are configured with various sensors and logic control such that the safety and efficacy of the devices and methods are enhanced. Such automatic features can contribute to advantageous ease-of-use, thereby making home treatments practical, convenient, and effective.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1 illustrates an example embodiment of an electroporation system that can treat dermatologic disorders and other conditions such as hyperhidrosis and cosmetic issues such as skin wrinkles with non-thermal irreversible or reversible electroporation in accordance with some embodiments provided herein.

Like reference numbers represent corresponding parts throughout.

DETAILED DESCRIPTION

This document describes devices and methods for treating skin disorders and other conditions such as hyperhidrosis, and cosmetic issues such as skin wrinkles. For example, this document describes devices and methods for treating dermatologic disorders, hyperhidrosis, and wrinkles using non-thermal irreversible or reversible electroporation. Such irreversible electroporation can be used to ablate keratinocyte neoplasms, such as seborrheic keratosis, and other non-keratinocyte derived neoplasms of the skin and adnexal structures and related structures in other anatomic sites. In some implementations, the devices and methods described herein can be used for therapy delivery for the treatment of early or pre-malignant skin cancers. In some embodiments, the devices and methods described herein can be used for treatment of hyperhidrosis. In some embodiments, the devices and methods described herein can be used for treatment of cosmetic issues (e.g., wrinkles), and can be synergistically used in combination with botulinum toxin (or other neurotoxins) in some cases.

Electroporation is a technology that applies pulsed electrical fields to a target tissue resulting in the formation of pores in the cellular membrane. Reversible electroporation occurs when the electrical field applied results in transient pore formation in the cellular membrane that the cell can later repair. Reversible electroporation does not result in cell death, but is utilized to deliver drugs or vaccination to target cells. Irreversible electroporation occurs when the magnitude of the electrical field applied causes the formation of permanent pores in the cell membrane resulting in death of the cell.

Electroporation involves the placement of a DC electrical field so as to modulate transmembrane potential and thereby cellular function without necessarily creating thermal damage (change in temperature). Keratinocyte modulation is uniquely suited for electroporation because of the multiple processes that basal cells (basal layer keratinocytes) need to undergo prior to their eventual placement as differentiate keratinocytes in the epidermis and whose unchecked proliferation gives rise to seborrheic keratosis.

As described further below, the pulsed electrical field of the irreversible electroporation can be delivered using various types of devices and methods. In some embodiments, electrodes, transcutaneous electrical patches, and/or an electro-conductive gel, liquid, semi-solid, or solid medium is used. Treatment enhancing agents can be a component of some embodiments of the devices and methods described herein. The devices and methods can also include sensors and controls that facilitate modification of the electrical field being delivered in order to adjust the magnitude, depth, time, and other parameters of the field being applied.

The inventors have developed a method for keratinocyte modulation (and for treating other conditions such as hyperhidrosis, and cosmetic issues such as skin wrinkles) that can include reversible or irreversible electroporation, and have in addition invented a unique system of delivery tools, modulatory electrical potential delivery sequences, algorithmic feedback controls for automated therapy delivery, and algorithmic incorporation of unique adjuvant therapy including anti-proliferative agents and inorganic electrolyte solutions (e.g., calcium chloride).

So as to avoid skeletal muscle stimulation, unwanted secretion from oil and sweat producing structures, unique bipolar focal field electroporation delivery tools are described herein. Accordingly, for example, if treating a lesion of manifest seborrheic keratosis, pressure sensitive electrodes are expanded over the lesion such that the exact geometry of the keratotic lesion is covered by the expandable electrode held or strapped over the lesion. As a result of electrode components, on the site of the lesion as well as over it, a three-dimensional electrical field can be deployed to variable depths at least equal to the height of the lesion.

Bipolar delivery of the electroporation sequence prevents far-field capture within the intentioned depth of field creation.

A calcium gradient from basal to outer epidermal cells is present in normal skin and integral to the keratinocyte differentiation process. The absence of this gradient, particularly with high levels of intracellular calcium within the surface differentiated keratinocytes, proliferation including excessive proliferation would likely not be possible. Through the unique electrode design, elution of electrolyte rich solutions including and specifically calcium chloride would have a triple modulatory effect on seborrheic keratosis, pre-seborrheic keratosis lesions, and keratinocyte function. Calcium chloride will diffuse in the presence of an electroporative current to the basal layers, negating the normal gradient. Further, voltage sensitive calcium triggered chloride release would also be negated. Further, since the stem cell-like basal keratinocytes are deeper, all other adjuvant therapies would be better and more targeted in terms of their delivery with the aid of electroporation. In some conditions, keratinocyte modulation is needed to be positive, for example, improving immune function, increasing vitamin D activity, or promoting hair follicular differentiation and growth. In these circumstances, intermittent reversible electroporation with hypotonic nonelectrolyte solutions may promote keratinocyte function, migration, and differentiation including into hair follicles as a treatment for local or generalize alopecia and hair loss.

Because seborrheic keratosis may be difficult to distinguish from other entities such as melanoma, actinic keratosis, sebaceous hyperplasia, basal or squamous cell carcinoma and occasionally nevi, electroporation with or without the adjuvant therapy would be expected to be palliative or curative for those conditions as well.

Since the keratinocytes are rich in calcium, the surface electrodes would be able to detect extracellular leakage of calcium from keratinocyte destruction either by means of evoke potentials or direct detection of free calcium. Thus, a feedback loop may be created where DC current is delivered until the release of calcium from the damaged surface keratinocytes such as those within the benign tumor of seborrheic keratosis is occurring. When a plateau of such release is made, then delivery cart be stopped. Further, electrodes at the peripheral will stop delivering current and creation of the field if no such calcium release is seen suggesting that those electrodes are beyond the edge of the lesion. Thus, the safety of energy delivery and exact localization of desired therapy is enabled and/or enhanced.

The devices and methods described herein can also be used for a variety of other applications, including for treatment of nevi, cosmetic purposes (e.g., wrinkle reduction), hair growth, treatment of other skin lesions, treatment of mucosal lesions (such as of the GI tract), treatment of vasculature lesions, and tumors elsewhere with the key elements being titratable energy delivery, unique electrode design, and the use of chemical and electrolyte adjuvants including calcium chloride. In some embodiments, the devices described herein can be mounted on, or used in conjunction with, an endoscope to access the GI tract (e.g., to treat irritable bowel syndrome, or chronic diarrhea), or the bronchus (e.g., to treat asthma) for example.

Referring to FIG. 1, an example system 100 can be used to treat dermatologic disorders using non-thermal irreversible or reversible electroporation. System 100 includes an electroporation applicator 110 that is connected to a controller 160 by a cable 180. Electroporation applicator 110 can be positioned against the skin of a user in order to deliver a treatment to a skin lesion (or other abnormality or issue) of the user. Controller 160 is pre-programmed and controllable by the user to deliver electroporation to the user's skin lesion in an automated or semi-automated fashion, including by using real-time feedback from one or more sensors during the electroporation delivery. Accordingly, such an arrangement can provide an electroporation treatment that is safe and effective. System 100 can deliver irreversible or reversible electroporation in accordance with the settings of controller 160.

Electroporation applicator 110 includes a head 112 that has a concave surface 113 that defines an internal space 114. When head 112 is placed against the user's skin, a vacuum can be drawn in internal space 114 such that the skin is drawn into internal space 114. In other words, head 112 can be used as a suction device. Suction can be generated by controller 160 (or a source of vacuum coupled thereto), transmitted through cable 180 to head 112, and to internal space 114 via one or more vacuum channels 115. The suction can stretch the skin/lesion and help to raise flat lesions. In some embodiments, the depth of internal space 114 is adjustable by the user. For example, in some embodiments head 112 is longitudinally compressible and expandable.

The diameter of internal space 114 at the open end of internal space 114 can be made to any suitable size. For example, in some embodiments the diameter of internal space 114 at the open end of internal space 114 is in a range from between 2 mm to 6 mm, or 4 mm to 8 mm, or 6 mm to 1 cm, or 8 mm to 1.2 cm, or 1 cm to 1.4 cm, or 1.2 cm to 1.6 cm, or 1.4 cm to 1.8 cm, or 1.6 cm to 2.0 cm, or 1.8 cm to 2.6 cm, or 2.2 cm to 3.0 cm, or 2.6 cm to 3.4 cm, or 3.0 cm to 3.8 cm, or 3.4 cm to 4.2 cm, or 3.8 cm to 5.0 cm, or 4.4 cm to 5.6 cm, or 5.0 cm to 6.2 cm, or 5.6 cm to 6.8 cm, or larger than 6.8 cm.

Around the periphery of internal space 114 are a plurality of protrusions 116. In some embodiments, there are two, three, four, five, six, seven, eight, nine, ten, eleven, twelve, thirteen, fourteen, fifteen, sixteen, seventeen, eighteen, nineteen, twenty or more than twenty protrusions 116. When head 112 is placed against the user's skin, protrusions 116 can indent the skin (e.g., around a lesion) without puncturing the skin. In some embodiments, the heights of the protrusions 116 are adjustable. In some embodiments, additionally or alternatively to protrusions 116, needles are included which can puncture the skin.

Each protrusion 116 can include an electrode for delivering electroporation. In embodiments that include needles instead of protrusions 116, the needles can include electrodes. In some embodiments, bipolar electroporation can be delivered using only the electrodes on protrusions 116. For example, in some embodiments multiple bipolar pairs of electrodes can be located on protrusions 116 around internal space 114. In some particular embodiments, bipolar pairs of electrodes are located on pairs of protrusions 116 that are 180 degrees opposite from each other around internal space 114.

In some embodiments, one or more electrodes 118 is/are located on concave surface 113. In such a case, one or more electrodes 118 can be "paired" with the electrodes on protrusions 116. For example, one or more electrodes 118 can be a cathode and the electrodes on protrusions 116 can be anodes. Or, one or more electrodes 118 can be an anode and the electrodes on protrusions 116 can be cathodes.

When delivering dermatologic treatment using system 100, the user can position head 112 in contact with the skin such that a lesion is located within the periphery defined by protrusions 116. Suction can be applied using controller 160, and the user can push head 112 onto the skin to create a seal around the lesion. In result, the lesion will be drawn into internal space 114. Then, controller 160 can activate bipolar electroporation (contemporaneously with the suction).

In some embodiments, inter-electrode impedance is monitored (by controller 160) between the electrodes on protrusions 116 and/or electrode(s) 118. In other words, in some embodiments the electroporation energy can be delivered on a pulsed direct current baseline, and multi-vector impedance measurements between the electrodes on protrusions 116 and/or electrode(s) 118 can be monitored (contemporaneously with the delivery of the pulsed electroporation energy). The detected impedance will tend to reflect characteristics of the tissue being treated. This detected impedance (and/or a measured trend in the impedance) can be used to control the electroporation energy delivery. In one such example, when detected impedance changes plateau, the delivery of the electroporation energy can be automatically ceased.

In some embodiments, irrigation within internal space 114 is also provided as part of the bipolar electroporation treatment from system 100. In some such cases, a fluid inlet and outlet can be defined by head 112. In some examples one or more pharmacological agents (e.g., for anti-cancer therapy) can be introduced using such irrigation. A second example purpose for irrigation is to administer calcium-containing liquid, which can manage some types of cell growths. A third example purpose for providing irrigation is to combine electroporation therapy (which heats tissue) in addition to cooling the tissue via the irrigate fluid.

In addition to the treatment of lesions, in some cases system 100 can be used to treat other conditions such as, but not limited to, wrinkles, striae or "stretch marks", acne, and various types of skin cancers.

Controller 160 will cycle and/or discontinue the delivery of the bipolar electroporation based on one or more factors that are programmed in controller 160 and/or detected by one or more feedback sensors in communication with controller 160. For example, in some embodiments one or more temperature detection devices (e.g., thermistor, thermostat, thermocouple, thermography) can be included to monitor the temperature of the lesion/skin. Such a temperature detector can also serve as a safety mechanism to shut off the system 100 when it reaches a certain temperature (e.g., a skin temperature above a particular threshold value). In some embodiments, changes in impedance between the electrodes can be monitored and used for controlling the delivery of electroporation. Poration can tend alter ion channels and change the impedance. If the cell membrane is compromised, they will leak intracellular fluid and the impedance will drop. This can be detected and converted to an impedance curve. Once the drop plateaus, electroporation is complete and delivery of the electroporation energy can be ceased by controller 160.

In some embodiments, one or more calcium sensors can be included as part of system 100 to determine apoptosis as a way of monitoring the state of electroporation (e.g., to determine when to stop the delivery of electroporation, modulate the intensity of the electroporation energy, and/or to change the delivery vector of the electroporation energy). In particular embodiments, electrograms can be used. In some such embodiments, first it would be determined that the skin has detectable electrical signals. If that is the case, when completely electroporated such electrical signals should disappear, signaling that electroporation delivery can be ceased.

In some embodiments, one or more humidity sensors can be included as a part of electroporation applicator 110 to detect perspiration from the skin. Such information can be useful for controlling the operations of system 100 because electroporation can, and is expected to cause sweat ducts to become temporarily impaired or dysfunctional. Therefore, for example, if a decrease in humidity is not detected by the humidity sensor, in response, electroporation energy delivery can be increased in intensity or duration until an expected decrease in humidity is detected by the humidity sensor. Further, if humidity does decrease as expected/desired, an end of the decreasing trend can be used as a signal to cease delivery of the electroporation energy in that area of the skin.

System 100 can use the electrodes as an electrical resistance-type moisture sensor that utilizes the relationship between the amount of moisture on the skin and the electrical resistance of the skin. In particular, the electrodes can operate on the principle that skin's resistance to the flow of electricity is lessened with increasing amounts of moisture such as perspiration. When the skin's GSR is lessened by perspiration, it can more readily conduct electricity and the flow of electricity can be detected by a monitoring circuit of system 100. Using these principles, the electrodes can be used to detect the presence of perspiration that may be determined to be at or above a threshold level amount of perspiration that is indicative of the delivery and efficacy of electroporation energy.

A camera can be included in some embodiments to monitor the redness of the skin. In some embodiments, only one such feedback mechanism is included in system 100. In particular embodiments, two or more such feedback mechanism are included in system 100.

In the depicted embodiment, controller 160 can include control circuitry such as multiple modules, devices, circuits, and sub-systems that function cooperatively to perform the operations of system 100 as described herein. For example, the control circuitry in controller 160 may include a combination of processor(s) and computer-readable memory (which may optionally store executable instructions configured to cause the control circuitry to perform the sensing, determination, and therapy operations described herein).

Processor(s) in controller 160 are suitable for the execution of one or more computer programs and include, by way of example, both general and special purpose microprocessors, and any one or more processors of any kind of digital computer. Such processor(s) can execute instructions, including the executable instructions that are stored in memory of controller 160. In some implementations, the processor(s) may be implemented as a chipset of chips that include separate and multiple analog and digital processors. The processor(s) may provide, for example, for coordination of the other components of system 100, such as control of delivery of electroporation energy from the bipolar electrodes, delivery of suction, and communications via a communication module with adjunct devices/systems.

Executable instructions of system 100 can be stored in memory, expansion memory, memory in processor, or in a combination thereof. The executable instructions can include instructions that, when executed, perform functions related to the operating systems of system 100 (e.g., operations of the user interface, coordination of intra-device module communications, control of the delivery of the DC electroporation energy from the electrodes, coordination and control of suction at head 112, and so on). In addition, in this embodiment the executable instructions include instructions that, when executed, perform one or more of the functions and methods described elsewhere herein in relation to physiological parameter monitoring, analysis of the monitored parametric data, alarming, and communications with other devices and systems, as well as clinicians or monitored technicians. In some implementations, the executable instructions, or portions thereof, can be received in a propagated signal, for example, via the communication modules and/or an antenna.

In some implementations, system 100 also includes an on-board power source. Such a power source can provide the electroporation energy, for example. In some embodiments, the power source includes an AC/DC converter/rectifier. In some embodiments, system 100 is powered by simply plugging a power cord of controller 160 into a 110 volt receptacle. In some embodiments, power source includes one or more batteries such as a non-rechargeable alkaline battery. In some embodiments, power source includes one or more rechargeable batteries such as a nickel-metal hydride, lithium ion, lithium polymer, or zinc oxide battery. In particular embodiments, a combination of the aforementioned types of batteries are used, and a combination of rechargeable and non-rechargeable batteries can be used.

To provide for interactions with a user, controller 160 can also include a user interface. The user interface includes devices and systems to receive inputs to system 100, and to provide outputs from system 100. For example, in some embodiments the user interface of controller 160 can include a display (in some embodiments the display is a touchscreen display), one or more buttons that can be soft keys or hard keys, one or more audio speakers, one or more lights, a microphone, a camera, tactile feedback mechanisms (e.g., vibratory alarm signals), and the like. Using such devices, the user interface can receive user input including voice input, touchscreen input, soft key inputs, and the like. The user interface can also provide outputs including audible alarms or messages, visual alarms or messages, tactile alarms or messages, differentiation of alarm types, and the like.

Other Embodiments of Electroporation Applicators

While system 100 was described above as including electroporation applicator 110 that comprises a suction cup-like head 112, other types of electroporation applicators can be used in an analogous manner. Such other types of electroporation applicators can include the following example embodiments. It should be understood that one or more features of any of the electroporation applicators described herein can be combined with one or more features of one or more of the other electroporation applicators described herein. In other words, hybrid electroporation applicators can be created by combining features described herein, and such hybrid embodiments are within the scope of this disclosure.

1) A loop or lasso device with circumferentially positioned electrodes can be used to encircle a lesion. Bipolar electroporation can be delivered by placing the loop/lasso around the lesion. In some embodiments, such a loop/lasso can be adjustable in size. In some cases, the loop/lasso can be tightened to capture/clamp the lesion, which can be particularly useful for raised lesions. Such a loop/lasso can include multiple embedded electrodes (e.g., by being a conductive wire with multiple spaced-apart insulated portions). In a related embodiment, the electroporation applicator can be configured like a basket with the loop/lasso at the open end of the basket. In some embodiments, electrodes can be located on the basket at other locations on the basket in addition to at/on the loop/lasso at the open end of the basket.

2) A donut-shaped device with circumferentially positioned electrodes can be used to encircle a lesion. A downward pressure can be applied against the skin using the donut-shaped device, which can cause the lesion to raise into the inner space defined by the donut-shaped device. In some embodiments, a strap can be attached to the donut-shaped device to secure it to the patient (and to apply downward pressure). In a related embodiment, the electroporation applicator can be configured to be worn around the user's neck (e.g., to treat loose skin like neck folds).

3) Clips or clamps that include electrodes can be used as electroporation applicators. Such clips/clamps can be attached onto the user's skin to pinch the skin (e.g., on and/or around a lesion). Bipolar electrodes can be located on the opposing arms of the clip/clamp so that electroporation is delivered to a lesion to which the clip/clamp is applied. The clip/clamp can advantageously tend to raise a flat lesion.

4) A patch device can provide a scaffold on which multiple microneedles are located. The patch can be applied onto the skin over a lesion, and electroporation can be applied. In some embodiments, the electroporation energy deliver from the patch device can be controlled by wireless communication (or wired communication). For example, a Dermatologist may do a video call with the patient such that the Dermatologist can view one or more lesions of the patient. The Dermatologist may instruct the patient to place the patch device in a particular location on the patient's skin. Then the Dermatologist may instruct the patient to turn on the delivery of electroporation energy and to communicate whether/when any pain results. In some embodiments, the patch device (and the other electroporation applicators described herein) can delivery electroporation of varying frequencies to blunt pain while giving another frequency of electroporation through another set of electrodes.

In some embodiments, a patch device can include an array of multiple surface contact electrodes that can be placed in contact with a skin surface. Such a device can have multiple anode/cathode quadrants or sub-divisions (e.g., 2 to 64 quadrants, or more) and can have a peripheral non-conductive (insulative) ridge. This type of device can be well suited for treatment of hyperhidrosis in some cases. In areas of the skin that are moist with sweat, the sweat on the skin can conduct the electroporation energy so as to treat those areas. Areas that are not moist will naturally not be treated because the impedance will be too high. Accordingly, the device is safe and can be used by a patient at home, for example. This form factor can be used to treat hyperhidrosis of the palms and soles, for example.

In some embodiments, the patch device with multiple surface electrodes can have a form factor like a wedge, or two wedges that are hinged together. Such a form factor can make the patch device well suited for use in the axilla (i.e., underarm area or armpit) of a patient to treat hyperhidrosis. In some embodiments, one wedge is the cathode and the second wedge is the anode. In particular embodiments, the wedge device is made of an absorbent or semi-absorbent material. In some embodiments, the two wedges that are hinged together can be inverted to create a clamp-like device.

5) A suction device (e.g., like electroporation applicator 110) with one or more dividers that form two or more internal spaces that can each deliver suction can be used to create an abrupt impedance change at the divider such that the electroporation energy will be focused toward the middle of the lesion. In some embodiments, the divider(s) physically deforms the tissue and in result changes the dynamics of the electroporation energy delivery in a desirable manner (e.g., to increase the focus/concentrate the electroporation energy density).

6) In some embodiments, a glove device (or sock device for feet) can be configured to deliver electroporation energy. In some examples, electrodes can be located internally on the glove and a patient can wear the glove to deliver electroporation to the patient's hand (e.g., to treat hyperhidrosis). In additional examples, the glove device can include external electrodes (e.g., on one or more of the fingertip(s) of the glove) and the patient can apply electroporation to other portions of the patient's body by wearing the glove device and positioning it over the lesion(s) to be treated on the other portions of the body. The rest of the glove, other than the electrodes, is insulated. Pressure can be applied to the lesion by the patient using the glove to enhance the electroporation delivery.

7) In some embodiments, a twisting motion can be applied via the electroporation applicator during the electroporation delivery. The twisting motion can cause the lesion to be raised, and the electroporation energy delivery can be enhanced accordingly (e.g., directed as desired). Suction can also be applied concurrent with the twisting motion in some embodiments.

Additional Optional Features

In some implementations, a band can be included to secure the electroporation applicator around an arm, leg, neck, or when expanded, head, chest, etc. In some implementations electrolytic gels can be used to diffuse the anode or/or cathode to varying extents to create a manipulatable field, which can be an important adjunct to simply varying the current intensity. This also provides a method to treat the skin disorders in a longitudinal manner as they spread or shrink, and thus the electrode coverage and electroporation area can be varied as desired. This is advantageous in some implementations because directional effects are undesired, i.e., akin to Botox injections, that tend to have concentrated effects at the site of injection.

In some implementations, system 100 can be configured for internal use. For example, the use of suction, the virtual capacitively coupled bipolar grid, etc., can be used as part of endoscopes for colonic and esophageal and other GI mucosa premalignant conditions. The same treatments as described above (but from inside out for internal use) could be performed for GI applications.

In some implementations, ECG monitoring is included. ECG detection algorithms can be used to shut off energy delivery whenever a tachycardia or wide complex arrhythmia is elicited, for safety as part of the feedback techniques.

The devices and methods can also include one or more sensors and controls that facilitate modification of the electrical field being delivered in order to adjust the magnitude, depth, time, and other parameters of the field being applied. In one such example, the devices can be equipped with a camera and the electroporation energy delivery can be automatically decreased or discontinued in response to a detection by the camera of increased redness of the skin (indicating early thermal injury or damage). In another example, the devices can be equipped with a sensor that detects sweat on the skin and the electroporation energy delivery can be automatically increased in response to detecting no decrease in the amount of sweat. Conversely, in some implementations plateauing of the decrease of sweat (i.e., a reduction in the rate of decrease of sweat) can be used to automatically decrease or cease electroporation energy delivery because when the sweat stops decreasing, this indicates that the desired effect of the electroporation energy has been achieved.

In some cases, uses of the devices described herein to treat cosmetic issues (e.g., skin wrinkles) can involve delivery of electroporation energy to target muscles (e.g., skeletal muscles) beneath the skin, while protecting the superficial layer of skin. That is, in some embodiments the electroporation energy field can be focused on deeper layers (below the skin). To achieve generate such an electroporation energy field, in some embodiments the devices include, over the electrodes, an outer insulative layer with small conductor elements (e.g., wires) strategically located to shunt energy from one area of the device to another. Such an arrangement will result in the creation of little or no electroporation energy field at the superficial level (e.g., adjacent to the partially shunted insulative layer). Greater field intensity will be created at deeper layers (farther away from the partially shunted insulative layer).

In some embodiments, the electrodes of the devices describe herein are projections that include an electrically conductive tip portion that are attached to an insulative proximal portion (which can also be shunted in some embodiments). That is, only the very tip portions of the projections are conductive electrodes. In some implementations, such indenting electrodes can be used as indenting electrodes (e.g., to indent skin when in use). In such a case, the skeletal muscles between two or more of the indenting electrodes will receive the electroporation energy field generated therebetween. In some embodiments, such electrodes can penetrate the skin surface rather than merely indenting it.

In particular embodiments, the indenting/penetrating electrodes that include an electrically conductive tip portion attached to an insulative proximal portion (which can also be shunted in some embodiments) can be differentially deflectable (e.g., manually mechanically by a pull-wire or the like, or automatically by the device) so that the delivery of electroporation energy can be focused and/or intensified. In some such embodiments, the electrodes can serve as sensing electrodes for skeletal muscle electrograms, which can be used as an electroporation feedback mechanism/signal. Where the skeletal muscle electrogram signals detect muscle activity, additional electroporation energy field application can be applied by deflection of particular electrodes to result in focusing of the electroporation energy field in the area(s) where the skeletal muscle electrogram activity is detected. The focused energy field application can continue to be delivered until the skeletal muscle electrograms are no longer detected (e.g., until the muscle is no longer viable).

For cosmetic treatments, in some implementations the devices and methods disclosed herein can be first applied using reversible electroporation to test the results. If the results are satisfactory, then a second step can be to use the devices and methods disclosed herein to deliver irreversible electroporation.

In some implementations, the devices and methods described here are advantageously used in combination with the delivery of neurotoxins (e.g., Botox®). With the delivery of neurotoxins alone, the treatment results are not immediately known because it takes time for the treatment to take effect, it may not be clear whether the injections are being delivered to the optimal muscle area(s), and the effects of the neurotoxins are temporary. Accordingly, the use of electroporation in combination with botulinum toxin delivery can be advantageous. Variations of the devices described herein can be made to deliver both botulinum toxin and electroporation in combination. For example, in some embodiments electrodes can be small needles (with the tip of the needle being the electrode) that define a lumen through which neurotoxins can be delivered. The electroporation field can be delivered (reversible and/or nonreversible) and the neurotoxins can be delivered sequentially, or concurrently, or both from the single device. Such a device can also include the functionality described above in which the electrodes can serve as sensing electrodes for skeletal muscle electrograms (as a feedback and control mechanism).

In another embodiment, the electrodes are indenting electrodes (i.e., electrodes that do not penetrate skin) while a substance containing neurotoxins (e.g., a gel) is also used to act as an iontophoresis. The electroporation delivered by the electrodes can drive the neurotoxins deeper into tissue of the skin, or below the skin surface. The electroporation field can be delivered (reversible and/or nonreversible) and the neurotoxins can be delivered sequentially, or concurrently, or both from the single device. Such a device can also include the functionality described above in which the electrodes can serve as sensing electrodes for skeletal muscle electrograms (as a feedback and control mechanism).

In another implementation, a substance containing neurotoxins can be applied to skin surface (e.g., as an ointment) and electrodes configured in a soft form factor (e.g., like a sponge) can be used to massage the substance into the skin while delivering electroporation energy. The electroporation delivered by the electrodes can drive the neurotoxins deeper into tissue of the skin, or below the skin surface. The electroporation field can be delivered (reversible and/or nonreversible) and the neurotoxins can be delivered sequentially, or concurrently, or both from the single device. Such a device can also include the functionality described above in which the electrodes can serve as sensing electrodes for skeletal muscle electrograms (as a feedback and control mechanism).

In another implementation, filler molecules (e.g., collagen, hyaluronic acid, etc.) can be driven into tissue of the skin, or below the skin surface, to add fullness to the skin using the devices and methods for electroporation described herein. In other words, such filler molecules can be administered using the devices and techniques that are described herein for delivering neurotoxins. In some embodiments, a single electroporation device can be used to deliver both neurotoxins and filler molecules.

Experimental Results

A prototype was created that successfully interfaces with the ANGIODYNAMICS NANOKNIFE system to deliver electrical charges. The device was tested on fresh non-frozen cadaveric skin with various electrical parameters. The non-invasive design required the use of saline to deliver the electrical pulses. A maximum voltage of 1050 V was consistently delivered with electrodes 1-4 as the positive electrodes and 6-9 as the negative electrodes. 10 pulses, 50 pulses, and 100 pulses were delivered. The treated tissue was observed and collected at various time points (e.g., 0 h, 4 h, 12 h, 24 h, 48 h). No changes were observed to the skin with the naked eye, however, on microscopic examination there was subepidermal separation with evidence of subcellular debris most confined to the area of separation. Interestingly, there eccrine ducts were effected with cleared out "bubbly" cytopathic changes. This confirms the potential of this device and/or electroporation in general of being a new treatment for hyperhidrosis.

Additionally, tests run by the inventors show that electroporation causes similar changes to nerves as does botulinum toxin. Botulinum toxin prevents the release of acetylcholine from the presynaptic neuron of neuromuscular junctions causing flaccid paralysis. Botulinum toxin is used throughout many fields and especially in dermatology for the treatment of numerous conditions including hyperhidrosis and glabellar/forehead lines. Regarding its use in hyperhidrosis, it blocks the nerve signals responsible for sweating. This also supports further confirmation of electroporation as a treatment for hyperhidrosis as it may cause similar effects as botulinum toxin on the nerves responsible for sweating. Since electroporation has similar effects as botulinum toxin, it is possible that non-thermal irreversible electroporation causes similar flaccid paralysis to muscles through the effects on motor nerves. With the increased use of botulinum toxin for the cosmetic treatment of glabellar and forehead lines, the devices and methods described herein (e.g., either non-invasive transcutaneous electroporation or an invasive needle based design) can be a valid alternative to Botox® for these indications.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying FIGURES do not necessarily require the particular order shown, or sequential order, to achieve desirable results. In certain implementations, multitasking and parallel processing may be advantageous.

What is claimed is:

1. A skin treatment system, comprising:

an electroporation applicator comprising:

a suction head with a concave surface defining an internal space; and a plurality of protrusions disposed around an external periphery of the internal space, each protrusion including a respective electrode mounted thereto;

one or more calcium sensors; and a controller in communication with the electroporation applicator [and the one or more calcium sensors] via one or more cables, the controller configured to concurrently: (1) provide direct current electroporation energy to the electrodes mounted on the protrusions and (11) draw a vacuum in the internal space of the suction head, the controller in communication with the one or more calcium sensors wherein the direct current electroporation energy provided to the electrodes is controlled based on feedback from the one or more calcium sensors.

2. The system of claim 1, further comprising one or more additional electrodes on the concave surface.

3. The system of claim 1, further comprising a temperature sensor coupled to the electroporation applicator and configured for measuring a temperature of skin to which the suction head is abutting.

4. The system of claim 1, further comprising a humidity sensor coupled to the electroporation applicator.

5. The system of claim 1, wherein the plurality of protrusions are height adjustable.

6. The system of claim 1, wherein the size of the internal space is adjustable.

7. The system of claim 1, further comprising a divider within the internal space and configured to split the internal space into two or more portions.

8. A method for treating a patient, the method comprising:
positioning a skin treatment system in contact with skin of the patient, the skin treatment system comprising:
an electroporation applicator comprising a suction head with a concave surface defining an internal space and a plurality of protrusions disposed around an external periphery of the internal space, each protrusion including a respective electrode mounted thereto;
one or more calcium sensors; and
a controller in communication with the electroporation applicator [and the one or more calcium sensors] via one or more cables, the controller configured to concurrently: (1) provide [, based on feedback from the one or more calcium sensors,] direct current electroporation energy to the electrodes mounted on the protrusions and (11) draw a vacuum in the internal space of the suction head, the controller in communication with the one or more calcium sensors wherein the direct current electroporation energy provided to the electrodes is controlled based on feedback from the one or more calcium sensors;
drawing vacuum in the internal space of the suction head such that skin of the patient is sucked into the internal space; and
while drawing the vacuum [and based on the feedback from the one or more calcium sensors,] delivering DC electroporation energy to the skin of the patient from the electrodes on the plurality of protrusions.

9. The method of claim 8, contemporaneously with drawing the vacuum and delivering the DC electroporation energy, measuring, by the controller, inter-electrode impedance.

10. The method of claim 9, further comprising modulating, by the controller and in response to the measured inter-electrode impedance, the delivery of the DC electroporation energy.

11. The method of claim 8, contemporaneously with drawing the vacuum and delivering the DC electroporation energy, measuring, by the controller, temperature of the skin of the patient.

12. The method of claim 11, further comprising modulating, by the controller and in response to the measured temperature of the skin of the patient, the delivery of the DC electroporation energy.

* * * * *

UNITED STATES PATENT AND TRADEMARK OFFICE
CERTIFICATE OF CORRECTION

PATENT NO. : 11,571,568 B2
APPLICATION NO. : 17/058419
DATED : February 7, 2023
INVENTOR(S) : Spencer A. Bezalel et al.

It is certified that error appears in the above-identified patent and that said Letters Patent is hereby corrected as shown below:

In the Claims

In Column 14, Line 67, In Claim 1, after applicator delete "[and the one or more calcium sensors]:".

In Column 15, Line 2, In Claim 1, delete "(1)" and insert -- (i) --.

In Column 15, Line 4, In Claim 1, delete "(11)" and insert -- (ii) --.

In Column 15, Line 34 (Approx.), In Claim 8, after applicator delete "[and the one or more calcium sensors]".

In Column 16, Line 2, In Claim 8, delete "(1)" and insert -- (i) --.

In Column 16, Lines 2-3, In Claim 8, after provide delete "[, based on feedback from the one or more calcium sensors,]".

In Column 16, Line 5, In Claim 8, delete "(11)" and insert -- (ii) --.

In Column 16, Lines 14-15, In Claim 8, after vacuum delete "[and based on the feedback from the one or more calcium sensors,]".

Signed and Sealed this
Fifteenth Day of October, 2024

Katherine Kelly Vidal
*Director of the United States Patent and Trademark Office*